US008481258B2

(12) United States Patent
Church et al.

(10) Patent No.: US 8,481,258 B2
(45) Date of Patent: Jul. 9, 2013

(54) METHODS AND COMPOUNDS FOR CHEMICAL LIGATION

(75) Inventors: George M. Church, Brookline, MA (US); A. Michael Sismour, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 336 days.

(21) Appl. No.: 12/628,518

(22) Filed: Dec. 1, 2009

(65) Prior Publication Data

US 2010/0092988 A1    Apr. 15, 2010

Related U.S. Application Data

(63) Continuation of application No. PCT/US2008/065523, filed on Jun. 2, 2008.

(60) Provisional application No. 60/941,805, filed on Jun. 4, 2007.

(51) Int. Cl.
*C12Q 1/68* (2006.01)
*C12P 19/34* (2006.01)
*C07H 21/00* (2006.01)
*C07H 21/02* (2006.01)
*C07H 21/04* (2006.01)

(52) U.S. Cl.
USPC ......... 435/6.1; 435/91.2; 536/22.1; 536/23.1; 536/24.3

(58) Field of Classification Search
USPC .................... 435/6.1, 91.2; 536/23.1, 24.3
See application file for complete search history.

(56) References Cited

U.S. PATENT DOCUMENTS

| | | | |
|---|---|---|---|
| 4,996,142 | A | 2/1991 | Al-Hakim et al. |
| 5,476,925 | A * | 12/1995 | Letsinger et al. ............ 536/23.1 |
| 5,599,922 | A * | 2/1997 | Gryaznov et al. ............ 536/25.3 |
| 5,750,341 | A | 5/1998 | Macevicz |
| 6,043,070 | A * | 3/2000 | Ellis et al. .................... 435/193 |
| 6,306,597 | B1 | 10/2001 | Macevicz |
| 6,376,246 | B1 * | 4/2002 | Crameri et al. ............... 435/440 |
| 2003/0207271 | A1 | 11/2003 | Holwitt et al. |
| 2008/0003571 | A1 * | 1/2008 | McKernan et al. ............... 435/6 |
| 2009/0191553 | A1 * | 7/2009 | Hendrickson .................... 435/6 |

OTHER PUBLICATIONS

Achilles et al., Kinetic model studies on the chemical ligation of oligonucleotides via hydrazone formation. Bioorganic & Medicinal Chemistry Letters 15(4) : 1229 (2005).*
Bailly et al., The use of diaminopurine to investigate structural properties of nucleic acids and molecular recognition between ligands and DNA. Nucleic Acids Research 26 (19) : 4309 (1998).*
Czlapinski et al., Template-directed assembly and characterization of metallosalen-DNA conjugates. Bioconjuge Chem.(2005) 16 (1):169 (2005).*
Dolinnaya et al. , Oligonucleotide circularization by template-directed chemical ligation. Nucleic Acids Research 21 (23) : 5403 (1993).*
Goodwin et al., JACS 114: 9197 (1992).*
Gryazov et al. , JACS 115: 3808 (1993).*
Gryazov et al. , Nucleic Acids Research 21 (6) : 1403 (1993).*
Harada et al., J. of Molecular Evolution 38 :558 (1994).*
Metelev et al., Nucleic Acids Research 29 (19) : 4062 (2001).*
Okamoto et al., Nucleic Acids Symposium Series 49 : 123(2005).*
Selvasekaran et al., Nucleic Acids Research 27 (2) : 624 (1999).*
Sokolova et al.232(1) 153 (1988).*
Zahn et al., JACS 119: 12,420 (1997).*
Shabarova et al.,Nucleic Acids Research. 19 (11) : 3067 (1991).*
Dolinnaya et al., Site-directed modification of DNA duplexes by chemical ligation. Nucleic Acids Research. 16 (9) : 3721 (1988).*
Dolinnaya et al., Nucleic Acids Research. 19 (11) : 3067 (1991).*
Shabarova et al., Nucleic Acids Research. 19 (15) : 4247 (1991).*
Dolinnaya et al. Russian Chemical Bulletin 45(8) :1787 (1996).*
Sokolova et al. FEB Letters 232 (1) : 153 (1988).*
James et al., Chemistry & Biology 4 :595 (1997).*
Gryaznov et al. Oligonucleotide N3' to P5' phosphoramidatres as antisense agents. Nucleic Acids Research 24(8) : 1508 (1996).*
Sokolova et al., Chemical reactions with DNA duplexes: Cyanogen bromide as an effective oligodeoxyribonucleotide coupling agent. FEBS Letters 231(1) :151 (1988).*
Shendure, J. et al., "Accurate Multiplex Polony Sequencing of an Evolved Bacterial Genome." Science 309, 1728 (2005).
Shendure, J. et al., "Advanced Sequencing Technologies:Methods and Goals." Nature Reviews, vol. 5, May 2004, 335.
Mitra, et al., "Fluorescent in Situ Sequencing on Polymerase Colonies." Analytical Biochemistry 320 (2003) 55-65.
Ronaghi, et al., "DNA Sequencing: A Sequencing Method Based on Real-Time Pyrophosphate." Science Jul. 17, 1998 pp. 363-365.
Brenner, et al., "Gene Expression Analysis by Massively Parallel Signature Sequencing (MPSS) on Microbead Arrays." Nature Biotechnology, vol. 18, Jun. 2000.
Scarpulla, et al., "Use of a New Retrieving Adaptor in the Cloning of a Synthetic Human Insulin A-Chain Gene." Analytical Biochemistry 121, 356-365 (1982).
Gupta, N.K., et al., "Studies on Polynucleotides, LXXXVII. The Joining of Short Deoxyribopolynucleotides by DNA-Joining Enzymes." Biochemistry, vol. 60, 1968.
James, et al., "Suprising Fidelity of Template-Directed Chemical Ligation of Oligonucleotides." Chemistry & Biology, Aug. 1997, 4:595-605.
Siddell, Stuart G., "RNA Hybridization to DNA Coupled with Cyanogen-Bromide-Activated Sephadex: The Purification of Polyoma Messenger RNA." Eur. J. Biochem. 92, 621-629 (1978).
Pall, et al., "Carbodiimide-Mediated Cross-Linking of RNA to Nylon Membranes Improves the Detection of siRNA, miRNA and piRNA by Northern Blot." Nucleic Acids Res. 35:60-, 2007.
Barre, et al.,"Unambiguous Demonstration of Triple-helix-Directed Gene Modification."Proc. Natl. Acad. Sci. USA. Mar. 28, 2000, vol. 97, No. 7, pp. 3084-3088.
Written Opinion of the International Searching Authority relating to corresponding PCT/US08/65523.
International Search Report relating to corresponding PCT/US08/65523.

* cited by examiner

*Primary Examiner* — Ethan C Whisenant
(74) *Attorney, Agent, or Firm* — Banner & Witcoff, Ltd.

(57) ABSTRACT

Compositions and methods for chemical ligation are provided. Methods for nucleic acid sequencing, nucleic acid assembly and nucleic acid synthesis are also provided.

55 Claims, 8 Drawing Sheets
(4 of 8 Drawing Sheet(s) Filed in Color)

1A

1B

1C

2A

2B

3A

3B

3C

3D

4A

4B

5A

5B

7A

7B

7C

7D

8A

8B

METHODS AND COMPOUNDS FOR CHEMICAL LIGATION

RELATED APPLICATIONS

This application is a continuation of PCT Application number PCT/US08/65523 designating the United States and filed on Jun. 2, 2008; which claims the benefit of U.S. provisional application No. 60/941,805; both of which are hereby incorporated herein by reference in their entireties.

STATEMENT OF GOVERNMENT INTERESTS

This application was funded in part by grant number DE-FG02-02ER63445, fund 148780, from the United States Department of Energy. The Government has certain rights in the invention.

FIELD OF THE INVENTION

The present invention relates to compounds and methods for chemically ligating nucleic acids.

BACKGROUND OF THE INVENTION

Known methods for 'next generation' (e.g., polony) sequencing use degenerate oligonucleotides and protein ligases to discriminate among oligonucleotides with perfect match at one or more positions relative to mismatched oligonucleotides (See, e.g., Shendure et al. (2005) Science 309: 1728; Applied Biosystems Solid; and Complete Genomics). Once ligated to an anchor oligonucleotide bound to an immobilized template, the solid phase is extensively washed to remove free fluor-oligonucleotides and then visualized with a digital camera. The oligonucleotides are typically labeled with fluorophores such that a given emission wavelength corresponds with given base(s) (e.g., A, C, G, T) at specific locations in the oligonucleotide bound to the template (e.g., unknown) DNA.

Methods employing degenerate oligonucleotides and protein ligases suffer from many disadvantages. In one approach, the coupling to each monomer goes to 50% completion in 0.15-2.5 hours and is, thus, too slow to be useful, perhaps in part because there is too little hybridization energy from a single base-pair (Griesang et al. (2006) Angew. Chem. Int. Ed. Engl. 45:6144). Another disadvantage of these art-known methods is that photocleavable protection chemistry requires intense irradiation with UV light, which can damage the DNA template to be sequenced after just a few deprotections.

SUMMARY OF THE INVENTION

The present invention is based in part on the discovery of novel reagents and methods for performing chemical ligation. Although protein ligases can, in principle, be engineered to accommodate a variety of template, oligonucleotide and anchor substrates, chemical ligation is far more versatile than protein ligases in accepting non-standard bases, backbone, and chemical bonds at the ligation position as well as throughout the probe oligonucleotide sequence. The chemical ligation reagents and methods described herein provide many advantages over traditional methods used for sequencing reactions, DNA assembly and the like.

In contrast with traditional ligase-based methods that query a single base at a time, the identity of multiple base pairs can be resolved in sequencing methods employing the chemical ligation reagents and methods described further herein. Further, the chemical ligation reagents and/or methods can utilize a no deprotection method for multiple (e.g., two rounds of ligation) and/or chemical deprotection method(s) (e.g., non-photochemical methods) for more than two rounds, thus eliminating the risk of UV damage to the DNA template.

In certain exemplary embodiments, a method of determining a nucleotide sequence of a reference oligonucleotide is provided. The method includes the steps of providing a reference oligonucleotide having an anchor primer bound thereto, providing a first probe oligonucleotide having a preactivated chemical ligation compound attached thereto, allowing the first probe oligonucleotide to hybridize to the reference oligonucleotide, and allowing the preactivated chemical ligation compound to mediate ligation between the hybridized first probe oligonucleotide and the anchor primer. In certain aspects, the preactivated chemical ligation compound is selected from the group consisting of a cyanogen bromide-based compound (e.g., a phosphocyanate such as N-Morpholino)Ethane Sulfonic Acid-cyanogen), a carbodiimide-based compound (e.g., an O-phospho-isocarbamide compound, such as phospho-1-Ethyl-3-[3-Dimethylaminopropyl]Carbodiimide), an amidate-based compound (e.g., a phosphoramidate that may optionally include an R group selected from the group consisting of pyridine, aniline, imidazole, ethanolamine, azaoxybenzotriazolide, N-oxysuccinimide and succinimide), and a phosphodiester mimetic (e.g., an imine). In certain aspects, the first probe oligonucleotide further includes one or more $S^2T$ molecules and/or one or more diaminopurines. In other aspects, one or more thymines of the first probe oligonucleotide are replaced by one or more $S^2T$ molecules. In yet other aspects, one or more adenines of the first probe oligonucleotide are replaced by one or more diaminopurines. In still other aspects, the method further includes the steps of providing a second probe oligonucleotide, allowing the second probe oligonucleotide to hybridize to the reference oligonucleotide, and allowing the preactivated chemical ligation compound to mediate ligation between the hybridized second probe oligonucleotide and the hybridized first probe oligonucleotide. The second probe oligonucleotide may optionally have a preactivated chemical ligation compound attached thereto.

In other exemplary embodiments, a method of assembling a polynucleotide sequence is provided. The method includes the steps of providing a plurality of overlapping oligonucleotides, at least a portion of which have a preactivated chemical ligation compound attached thereto, allowing hybridization of at least a portion of the overlapping oligonucleotides to each other, and allowing the preactivated chemical ligation compounds to mediate ligation between adjacent 5' and 3' ends of hybridized oligonucleotides to assemble a polynucleotide sequence. In certain aspects, the polynucleotide sequence is DNA such as, for example, one or more of a vector, a gene, a gene fragment, an exon, an intron or an intergenic DNA sequence.

In other exemplary embodiments, a method of synthesizing a polynucleotide sequence is provided. The method includes the steps of providing a first oligonucleotide having a preactivated chemical ligation compound attached thereto, providing a second oligonucleotide, and allowing the preactivated chemical ligation compound to mediate ligation between the first oligonucleotide and the second oligonucleotide. In certain aspects, the method further includes the step of allowing the first oligonucleotide to bind a reference oligonucleotide. In other aspects, the reference oligonucleotide is attached to a substrate.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which.

DETAILED DESCRIPTION

Figure 1:
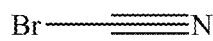
FIGS. 1A-1C depict certain nitrogen compounds useful in chemical ligation reactions. A) cyanogen bromide (CNBr). B) MES-CN (MES=2-(N-Morpholino)Ethane Sulfonic Acid). C) a 3' phosphocyanate compound.
Figure 1:
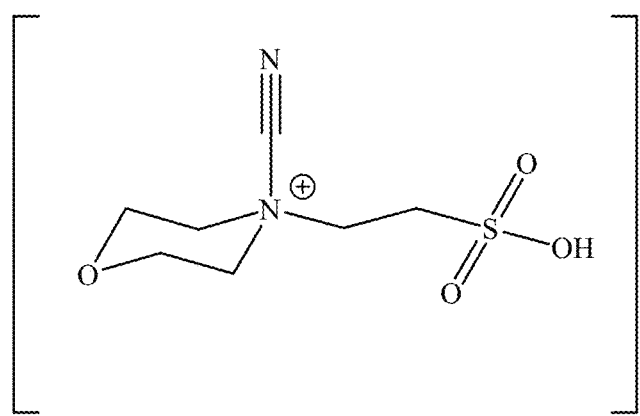
Figure 1:
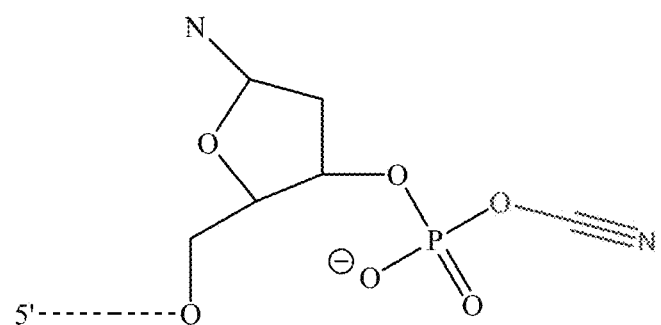

The principles of the present invention may be applied with particular advantage to determine the identity of oligonucleotide sequences. The principles of the present invention may further be applied with particular advantage to assemble and/or synthesize polynucleotide sequences.

DNA ligation is the process of joining together two DNA molecule ends (either from the same or different molecules). Specifically, it typically involves creating a phosphodiester bond between the 3' hydroxyl of one nucleotide and the 5' phosphate of another, and is usually catalyzed by a DNA ligase. As used herein, the term "chemical ligation compound" refers to a variety of chemical compounds that can be used, alone or in combination, to mediate one or more chemical ligation reactions. Useful c chemical ligation compounds include, but are not limited to: 1) cyanogen bromide-based compounds (e.g., phosphocyanates such as MES-CN (MES=2-(N-Morpholino)Ethane Sulfonic Acid) and the like); 2) carbodiimide-based compounds (e.g., O-phosphoisocarbamide compounds such as phospho-EDC; 3) amidate-based compounds (e.g., phosphoramidates); and 4) phosphodiester mimetics (e.g., aldehydes generated by periodate, Schiff's base intermediates and the like). Chemical ligation compounds and reactions including one or more of them are described further herein.

In certain exemplary embodiments, an oligonucleotide sequence having one or more preactivated phosphates is provided. As used herein, the term "preactivated phosphate" refers to a nucleotide or an oligonucleotide having a phosphate group (e.g., at the 5' and/or 3' end of the nucleotide or oligonucleotide) available for covalently binding a nucleotide and/or oligonucleotide sequence having an available non-phosphate reactive group, e.g., an hydroxyl, a sulfhydryl, an amine or the like.

As used herein, the terms "nucleic acid molecule," "nucleic acid sequence," "nucleic acid fragment," "oligonucleotide" and "polynucleotide" are used interchangeably and are intended to include, but not limited to, a polymeric form of nucleotides that may have various lengths, either deoxyribonucleotides or ribonucleotides, or analogs thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, ribozymes, small interfering RNA (siRNA), cDNA, recombinant polynucleotides, branched polynucleotides, plasmids, vectors, isolated DNA of a sequence, isolated RNA of a sequence, nucleic acid probes, and primers. Oligonucleotides useful in the methods described herein may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Examples of modified nucleotides include, but are not limited to diaminopurine, S$^2$T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

In accordance with certain examples, methods of sequencing nucleic acid sequences by hybridization using one or more of the chemical ligation compounds and/or chemical ligation methods described herein are provided. General sequencing methods known in the art, such as sequencing by extension with reversible terminators, fluorescent in situ sequencing (FISSEQ), pyrosequencing, massively parallel signature sequencing (MPSS), solid sequencing (Applied Biosystems, Foster city, Calif.), and the like (described in Shendure et al. (2004) *Nat. Rev.* 5:335; reversible termination methods: U.S. Pat. Nos. 5,750,341 and 6,306,597; FISSEQ: Mitra et al. (2003) *Anal. Biochem.* 320:55; Pyrosequencing: Ronaghi et al. (1998) *Science* 281:363; MPSS: Brenner et al. (2000) *Nat. Biotech.* 18:630), are suitable for use with the chemical ligation compounds and assays described herein.

In exemplary embodiments, a plurality of overlapping oligonucleotide sequences will be used to assemble a larger polynucleotide sequence, such as DNA. The plurality of overlapping oligonucleotides can be exposed to conditions that allow hybridization to form duplexes. For example, oligonucleotide sequences may be exposed to hybridization conditions followed by ligation using one or more chemical ligation reagents and/or chemical ligation methods described further herein. Methods of ligating preformed duplexes using DNA ligases are well-known in the art (See Scarpulla et al. (1982) *Anal. Biochem.* 121:356, and Gupta et al. (1968) *Proc. Natl. Acad. Sci. USA* 60:1338).

Oligonucleotide sequences may be isolated from natural sources or purchased from commercial sources. In certain exemplary embodiments, oligonucleotide sequences may be prepared using one or more of the chemical ligation compounds and/or the chemical ligation methods described herein. Oligonucleotide sequences may also be prepared by any suitable method, e.g., the phosphoramidite method described by Beaucage and Carruthers ((1981) *Tetrahedron Lett.* 22: 1859) or the triester method according to Matteucci et al. (1981) *J. Am. Chem. Soc.* 103:3185), or by other chemical methods using either a commercial automated oligonucleotide synthesizer or high-throughput, high-density array methods known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

In certain exemplary embodiments, oligonucleotide sequences may be prepared using a variety of microarray technologies known in the art. Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) *Proc. Natl. Acad. Sci. U.S.A.* 93:13555; *Synthetic DNA Arrays* In Genetic Engineering, Vol. 20:111, Plenum Press (1998); Duggan et al. (1999) *Nat. Genet.* S21:10; *Microarrays: Making Them and Using Them* In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Application Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597.

In certain exemplary embodiments, one or more oligonucleotide sequences described herein are immobilized on a support. Suitable supports include, but are not limited to, slides, beads, chips, particles, strands, gels, sheets, tubing, spheres, containers, capillaries, pads, slices, films, plates and the like. In various embodiments, the solid supports may be biological, nonbiological, organic, inorganic, or combinations thereof. When using supports that are substantially planar, the support may be physically separated into regions, for example, with trenches, grooves, wells, or chemical barriers (e.g., hydrophobic coatings, etc.).

In certain exemplary embodiments, a support is a microarray. As used herein, the term "microarray" refers in one embodiment to a type of assay that comprises a solid phase support having a substantially planar surface on which there is an array of spatially defined non-overlapping regions or sites that each contain an immobilized hybridization probe. "Substantially planar" means that features or objects of interest, such as probe sites, on a surface may occupy a volume that extends above or below a surface and whose dimensions are small relative to the dimensions of the surface. For example, beads disposed on the face of a fiber optic bundle create a substantially planar surface of probe sites, or oligonucleotides disposed or synthesized on a porous planar substrate creates a substantially planar surface. Spatially defined sites may additionally be "addressable" in that its location and the identity of the immobilized probe at that location are known or determinable.

Probes immobilized on microarrays include nucleic acids that are generated in or from an assay reaction. Typically, the oligonucleotides or polynucleotides on microarrays are single stranded and are covalently attached to the solid phase support, usually by a 5'-end or a 3'-end. The density of non-overlapping regions containing nucleic acids in a microarray is typically greater than 100 per $cm^2$, and more typically, greater than 1000 per $cm^2$. Microarray technology relating to nucleic acid probes is reviewed in the following exemplary references: Schena, Editor, *Microarrays: A Practical Approach* (IRL Press, Oxford, 2000); Southern, *Current Opin. Chem. Biol.*, 2: 404-410 (1998); *Nature Genetics Supplement*, 21:1-60 (1999); and Fodor et al, U.S. Pat. Nos. 5,424,186; 5,445,934; and 5,744,305.

Methods of immobilizing oligonucleotides to a support are known in the art (beads: Dressman et al. (2003) *Proc. Natl. Acad. Sci. USA* 100:8817, Brenner et al. (2000) *Nat. Biotech.* 18:630, Albretsen et al. (1990) *Anal. Biochem.* 189:40, and Lang et al. *Nucleic Acids Res.* (1988) 16:10861; nitrocellulose: Ranki et al. (1983) *Gene* 21:77; cellulose: Goldkorn (1986) *Nucleic Acids Res.* 14:9171; polystyrene: Ruth et al. (1987) Conference of Therapeutic and Diagnostic Applications of Synthetic Nucleic Acids, Cambridge U.K.; teflon-acrylamide: Duncan et al. (1988) *Anal. Biochem.* 169:104; polypropylene: Polsky-Cynkin et al. (1985) *Clin. Chem.* 31:1438; nylon: Van Ness et al. (1991) *Nucleic Acids Res.* 19:3345; agarose: Polsky-Cynkin et al., *Clin. Chem.* (1985) 31:1438; and sephacryl: Langdale et al. (1985) *Gene* 36:201; latex: Wolf et al. (1987) *Nucleic Acids Res.* 15:2911).

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell,* 3d edition, Garland Publishing, 1994.

In certain exemplary embodiments, a detectable label can be used to detect one or more nucleotides and/or oligonucleotides described herein. Examples of detectable markers include various radioactive moieties, enzymes, prosthetic groups, fluorescent markers, luminescent markers, bioluminescent markers, metal particles, protein-protein binding pairs, protein-antibody binding pairs and the like. Examples of fluorescent proteins include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorinidases, phosphatases, peroxidases, cholinesterases and the like. Identifiable markers also include radioactive compounds such as $^{125}I$, $^{35}S$, $^{14}C$, or $^3H$. Identifiable markers are commercially available from a variety of sources.

Fluorescent labels and their attachment to nucleotides and/or oligonucleotides are described in many reviews, including Haugland, *Handbook of Fluorescent Probes and Research Chemicals,* Ninth Edition (Molecular Probes, Inc., Eugene, 2002); Keller and Manak, DNA Probes, 2nd Edition (Stockton Press, New York, 1993); Eckstein, editor, *Oligonucleotides and Analogues: A Practical Approach* (IRL Press, Oxford, 1991); and Wetmur, *Critical Reviews in Biochemistry and Molecular Biology,* 26:227-259 (1991). Particular methodologies applicable to the invention are disclosed in the following sample of references: Fung et al., U.S. Pat. No. 4,757,141; Hobbs, Jr., et al. U.S. Pat. No. 5,151,507; Cruickshank, U.S. Pat. No. 5,091,519. In one aspect, one or more fluorescent dyes are used as labels for labeled target sequences, e.g., as disclosed by Menchen et al., U.S. Pat. No. 5,188,934 (4,7-dichlorofluorscein dyes); Begot et al., U.S. Pat. No. 5,366,860 (spectrally resolvable rhodamine dyes); Lee et al., U.S. Pat. No. 5,847,162 (4,7-dichlororhodamine dyes); Khanna et al., U.S. Pat. No. 4,318,846 (ether-substituted fluorescein dyes); Lee et al., U.S. Pat. No. 5,800,996 (energy transfer dyes); Lee et al., U.S. Pat. No. 5,066,580 (xanthine dyes): Mathies et al., U.S. Pat. No. 5,688,648 (energy transfer dyes); and the like. Labelling can also be carried out with quantum dots, as disclosed in the following patents and patent publications: U.S. Pat. Nos. 6,322,901; 6,576,291; 6,423,551; 6,251,303; 6,319,426; 6,426,513; 6,444,143; 5,990,479; 6,207,392; 2002/0045045; and 2003/0017264. As used herein, the term "fluorescent label" includes a signaling moiety that conveys information through the fluorescent absorption and/or emission properties of one or more molecules. Such fluorescent properties include fluorescence intensity, fluorescence lifetime, emission spectrum characteristics, energy transfer, and the like.

Commercially available fluorescent nucleotide analogues readily incorporated into nucleotide and/or oligonucleotide sequences include, but are not limited to, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHODAMINE GREEN™-5-dUTP, OREGON GREENR™ 488-5-dUTP, TEXAS RED™-12-dUTP, BODIPY TM 630/650-14-dUTP, BODIPY TM 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY TM FL-14-UTP, BODIPY TMR-14-UTP, BODIPY TM TR-14-UTP, RHODAMINE GREEN™-5-UTP, ALEXA FLUOR™ 488-5-UTP, LEXA FLUOR™ 546-14-UTP (Molecular Probes, Inc. Eugene, Oreg.) and the like. Protocols are known in the art for custom synthesis of nucleotides having other fluorophores (See, Henegariu et al. (2000) *Nature Biotechnol.* 18:345).

Other fluorophores available for post-synthetic attachment include, but are not limited to, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red (available from Molecular Probes, Inc., Eugene, Oreg.), Cy2, Cy3.5, Cy5.5, Cy7 (Amersham Biosciences, Piscataway, N.J.) and the like. FRET tandem fluorophores may also be used, including, but not limited to, PerCP-Cy5.5, PE-Cy5, PE-Cy5.5, PE-Cy7, PE-Texas Red, APC-Cy7, PE-Alexa dyes (610, 647, 680), APC-Alexa dyes and the like.

Metallic silver or gold particles may be used to enhance signal from fluorescently labeled nucleotide and/or oligonucleotide sequences (Lakowicz et al. (2003) *BioTechniques* 34:62).

Biotin, or a derivative thereof, may also be used as a label on a nucleotide and/or an oligonucleotide sequence, and subsequently bound by a detectably labeled avidin/streptavidin derivative (e.g. phycoerythrin-conjugated streptavidin), or a detectably labeled anti-biotin antibody. Digoxigenin may be incorporated as a label and subsequently bound by a detectably labeled anti-digoxigenin antibody (e.g. fluoresceinated anti-digoxigenin). An aminoallyl-dUTP residue may be incorporated into an oligonucleotide sequence and subsequently coupled to an N-hydroxy succinimide (NHS) derivatized fluorescent dye. In general, any member of a conjugate pair may be incorporated into a detection oligonucleotide provided that a detectably labeled conjugate partner can be bound to permit detection. As used herein, the term antibody refers to an antibody molecule of any class, or any subfragment thereof, such as an Fab.

Other suitable labels for an oligonucleotide sequence may include fluorescein (FAM), digoxigenin, dinitrophenol (DNP), dansyl, biotin, bromodeoxyuridine (BrdU), hexahistidine (6×His), phosphor-amino acids (e.g. P-tyr, P-ser, P-thr) and the like. In one embodiment the following hapten/antibody pairs are used for detection, in which each of the antibodies is derivatized with a detectable label: biotin/α-biotin, digoxigenin/α-digoxigenin, dinitrophenol (DNP)/α-DNP, 5-Carboxyfluorescein (FAM)/α-FAM.

In certain exemplary embodiments, a nucleotide and/or an oligonucleotide sequence can be indirectly labeled, especially with a hapten that is then bound by a capture agent, e.g., as disclosed in Holtke et al., U.S. Pat. Nos. 5,344,757; 5,702,888; and 5,354,657; Huber et al., U.S. Pat. No. 5,198,537; Miyoshi, U.S. Pat. No. 4,849,336; Misiura and Gait, PCT publication WO 91/17160; and the like. Many different hapten-capture agent pairs are available for use. Exemplary haptens include, but are not limited to, biotin, des-biotin and other derivatives, dinitrophenol, dansyl, fluorescein, CYS, digoxigenin and the like. For biotin, a capture agent may be avidin, streptavidin, or antibodies. Antibodies may be used as capture agents for the other haptens (many dye-antibody pairs being commercially available, e.g., Molecular Probes, Eugene, Oreg.).

In certain exemplary embodiments, a first (e.g., probe) oligonucleotide sequence is annealed to a second (e.g., reference) oligonucleotide sequence. The terms "annealing" and "hybridization," as used herein, are used interchangeably to mean the formation of a stable duplex. In one aspect, stable duplex means that a duplex structure is not destroyed by a stringent wash, e.g., conditions including temperature of about 5° C. less that the $T_m$ of a strand of the duplex and low monovalent salt concentration, e.g., less than 0.2 M, or less than 0.1 M. The term "perfectly matched," when used in reference to a duplex means that the polynucleotide and/or oligonucleotide strands making up the duplex form a double stranded structure with one another such that every nucleotide in each strand undergoes Watson-Crick base pairing with a nucleotide in the other strand. The term "duplex" includes, but is not limited to, the pairing of nucleoside analogs, such as deoxyinosine, nucleosides with 2-aminopurine bases, PNAs, and the like, that may be employed. A "mismatch" in a duplex between two oligonucleotides means that a pair of nucleotides in the duplex fails to undergo Watson-Crick bonding.

The term "hybridization," as used herein, refers to the process in which two single-stranded oligonucleotides bind non-covalently to form a stable double-stranded oligonucleotide. The term "hybridization" may also refer to triple-stranded hybridization. The resulting (usually) double-stranded polynucleotide is a "hybrid" or "duplex."

As used herein, the term "hybridization conditions," will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will specifically hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

Generally, stringent conditions are selected to be about 5° C. lower than the $T_m$ for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual,* 2nd Ed. Cold Spring Harbor Press (1989) and Anderson *Nucleic Acid Hybridization,* $1^{st}$ Ed., BIOS Scientific Publishers Limited (1999). As used herein, the terms "hybridizing specifically to" or "specifically hybridizing to" or similar terms refer to the binding, duplexing, or hybridizing of a molecule substantially to a particular nucleotide sequence or sequences under stringent conditions.

As used herein, the term "hybridization-based assay" is intended to refer to an assay that relies on the formation of a stable complex as the result of a specific binding event. In one aspect, a hybridization-based assay means any assay that relies on the formation of a stable duplex or triplex between a probe and a target nucleotide sequence for detecting or measuring such a sequence. A "probe" in reference to a hybridization-based assay refers to an oligonucleotide sequence that has a sequence that is capable of forming a stable hybrid (or triplex) with its complement in a target nucleic acid and that is capable of being detected, either directly or indirectly.

The following examples are set forth as being representative of the present invention. These examples are not to be construed as limiting the scope of the invention as these and other equivalent embodiments will be apparent in view of the present disclosure, figures, tables, and accompanying claims. The contents of all references, patents and published patent applications cited throughout this application are hereby incorporated by reference in their entirety for all purposes.

Example I

Four Classes of Fast, Accurate Chemical Reactions

Four classes of fast and accurate chemical reactions have been identified: 1) cyanogen bromide-based reactions; 2) carbodiimide-based reactions; 3) amidate-based reactions; and 4) phosphodiester mimetic-based reactions. These classes are suitable for use in a variety of methods that can utilize ligations including, but not limited to, sequencing by chemical ligation, synthesis of oligonucleotide sequences and assembly of oligonucleotide sequences.

Figure 2:
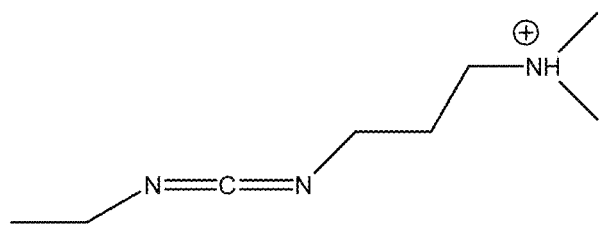
FIGS. 2A-2B depict carbodiimide compounds. A) EDC (1-Ethyl-3-[3-Dimethylaminopropyl]Carboiimide. B) a 3' phospho-EDC compound.
Figure 2:
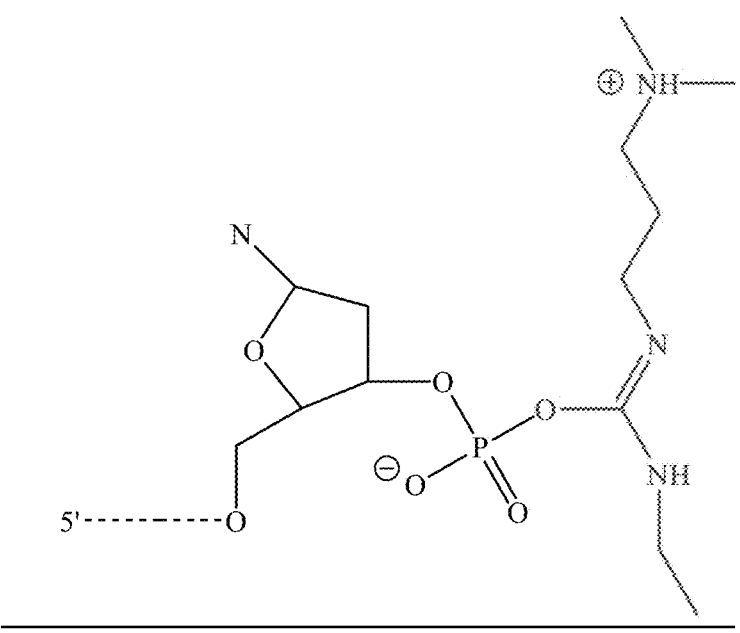
Figure 3:
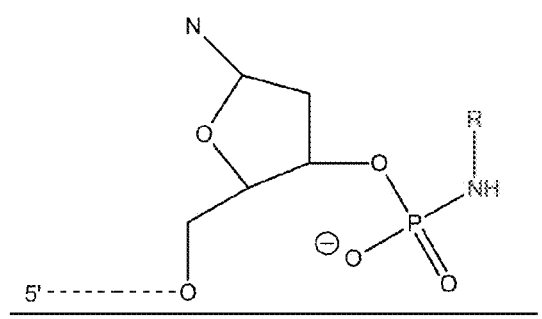
FIGS. 3A-3D depict phosphoramidate compounds. A) a 3' phosphoramidate compound. B) a 5' phosphoramidate compound. C) a 3' phosphoramidate compound. D) a variety of R groups useful with phosphoramidate compounds such as, for example, the compounds depicted in A)-C). Left to right: pyridine, aniline, imidazole, ethanolamine, azaoxybenzotriazolide, N-oxysuccinimide and succinimide.
Figure 3:
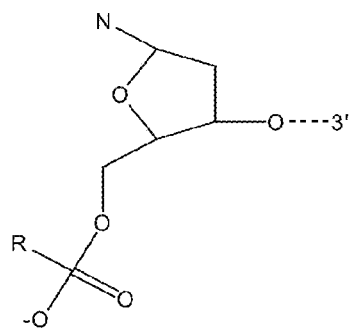
Figure 3:
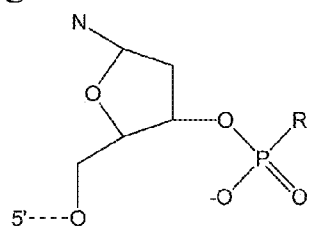
Figure 3:
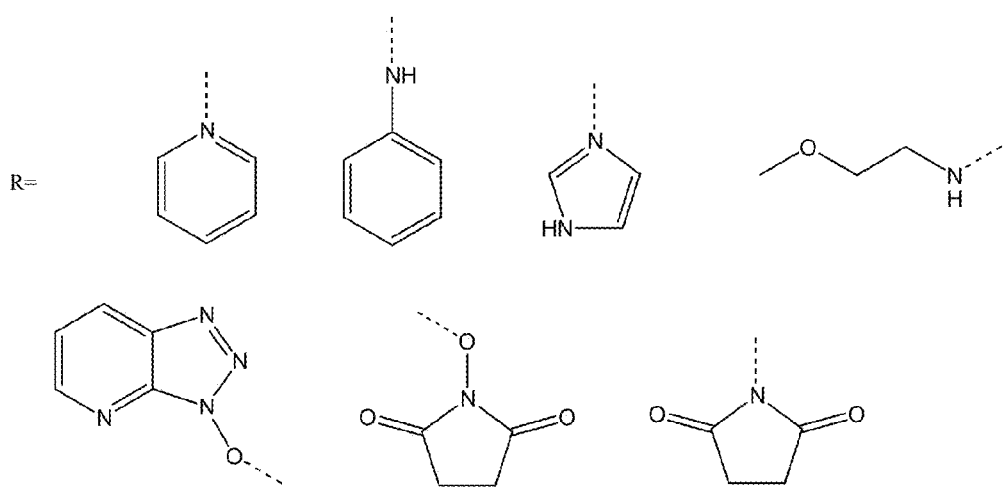
Figure 4:
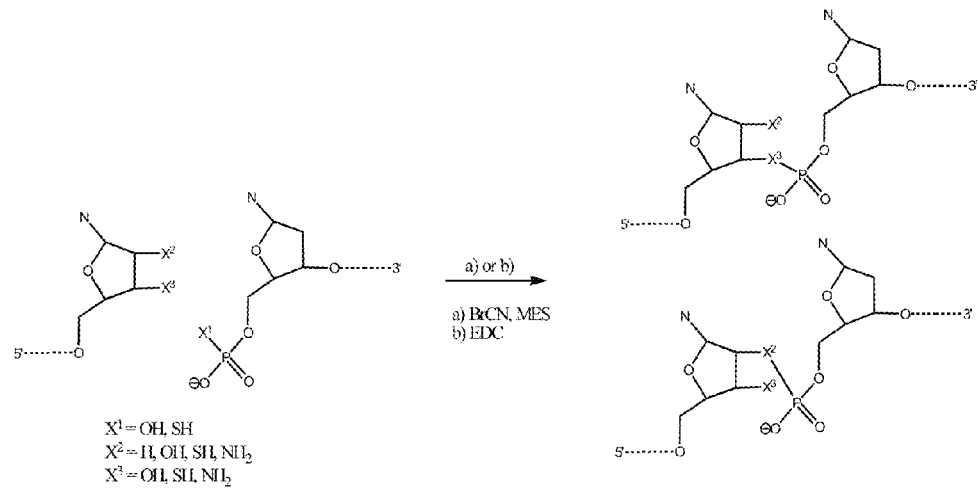
FIGS. 4A-4B depict cyanogen bromide and EDC chemical ligation reactions. These reactions were very fast (a few seconds) and were limited only by the hybridization kinetics in a complex mixture of 6-mer to 9-mer oligonucleotides.
Figure 4:
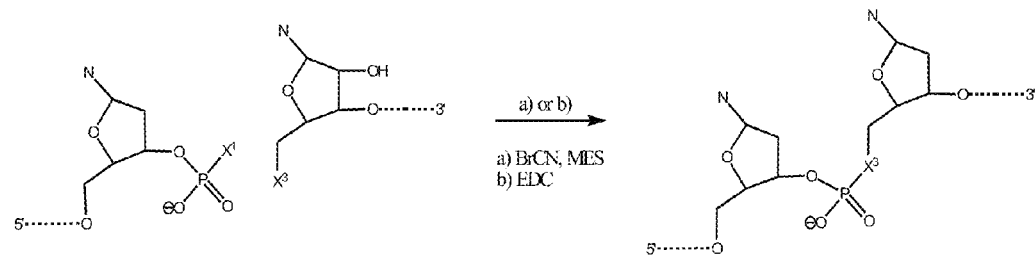
Figure 6:
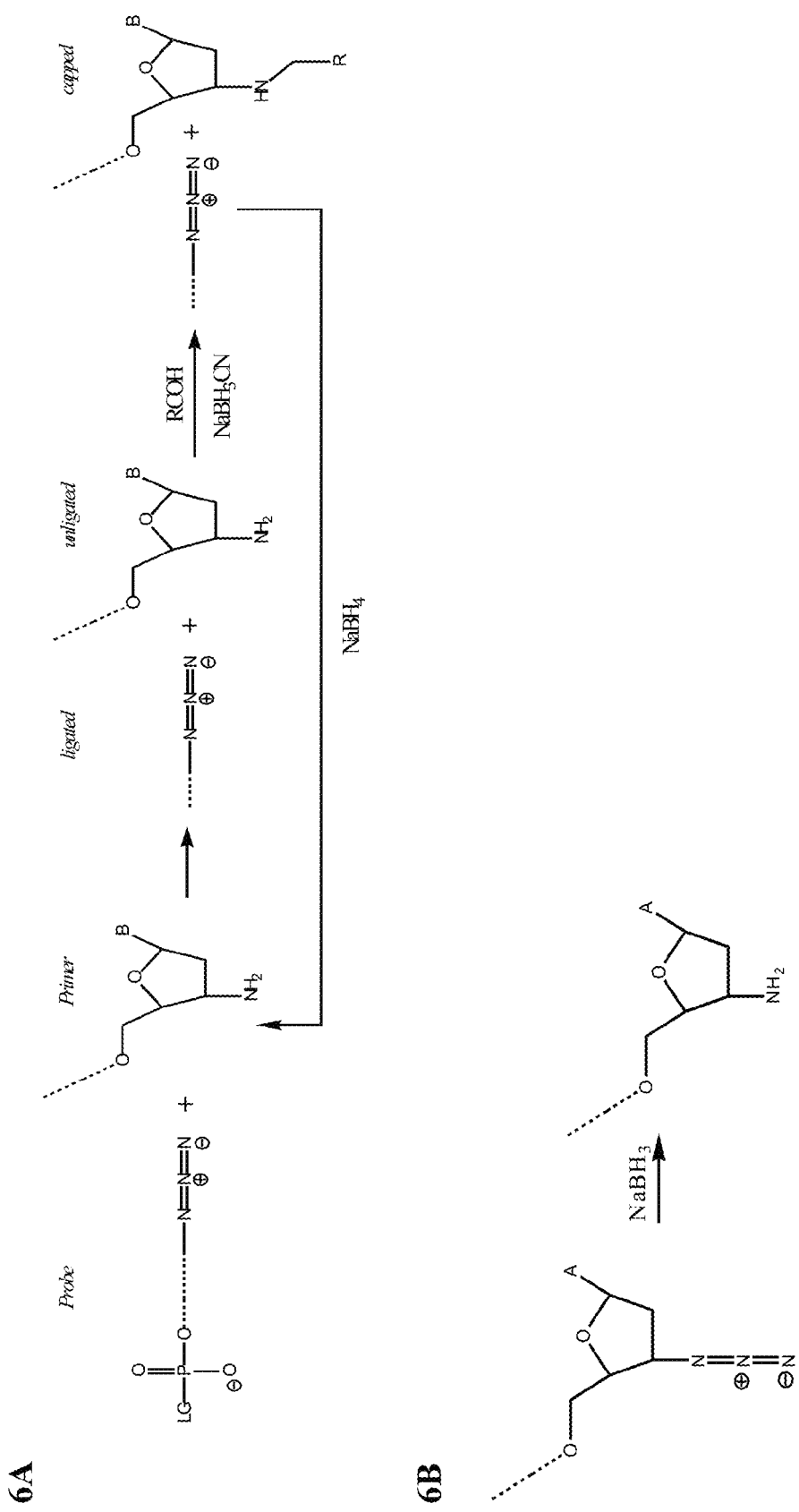
FIGS. 6A-6B depict reaction schemes for the ligation, capping of non-reacted primers, and deprotection of 3'-azido probes for subsequent ligations. The reaction scheme (A) includes, from left to right, the ligation of a 3'-amino primer oligonucleotide with an oligonucleotide probe, followed by capping any non-reacted 3'-amino primer oligonucleotides by addition of excess aldehyde for an imine that is subsequently reduced to an amide using NaCNBH$_3$. This was followed by deprotection of the 3'-azido probe oligonucleotide using NaBH$_4$ in the presence of CoCl$_2$ (A, B). This capping/deprotection scheme can be repeated for subsequent ligations of 3'-azido probe oligonucleotides.

Cyanogen bromide-based reactions (FIG. 1) and carbodiimide-based reactions (FIG. 2) were used to perform sequencing by ligation reactions. The reactions proceeded in a very fast manner (i.e., on the order of a few seconds). The reaction rate was limited only by hybridization kinetics in a complex mixture of 6-mer to 9-mer oligonucleotide sequences. Cyanogen bromide-based and carbodiimide-based chemical ligation reactions are depicted in FIG. 4. Amidate-based reactions and compounds useful in such reactions are described in FIG. 3. Reaction schemes are depicted in FIG. 6.

Example II

Phosphodiester Mimetics

Figure 7:
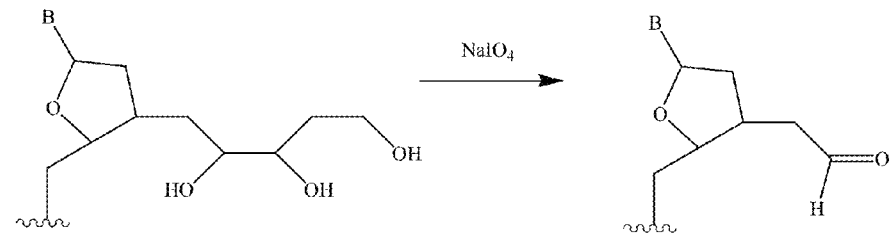
FIGS. 7A-7D depict various phosphodiester mimetic schemes. Aldehyde functional groups can be formed at the 3' terminus of an oligonucleotide using an oligonucleotide containing a (A) 3' alkyl vicinal diol or (B) an oligonucleotide terminated at the 3' end in a nucleotide (as opposed to a deoxynucleotide) by oxidation with periodate. Such aldehydes can form (C) imines with oligonucleotides containing a 5' amine. In addition to such imine phosphodiester mimetics, (D) the vicinal diol of oligonucleotides terminated at the 3' end in a nucleotide (as opposed to a deoxynucleotide) can react with cyanogen bromide to form a hydroxy-isocyanate (left most molecule) that can further react with a 5'-OH on an oligonucleotide to form the hydroxy-isocyanate phosphodiester mimetic.
Figure 7:
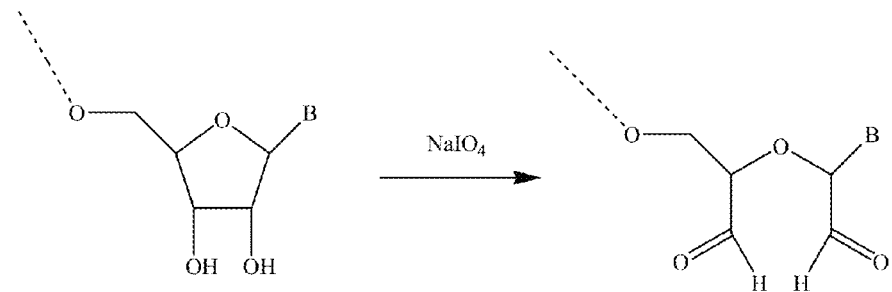
Figure 7:
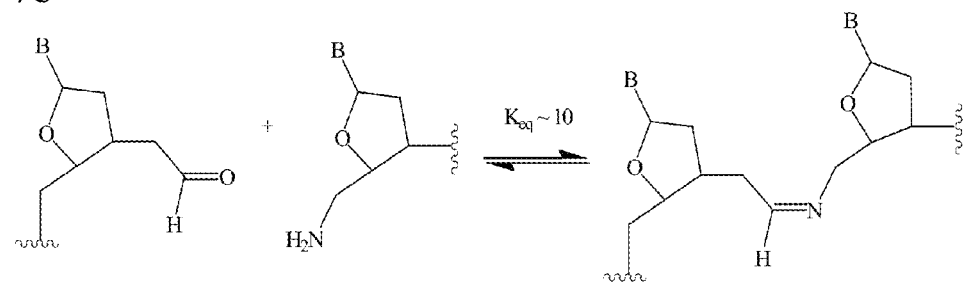
Figure 7:
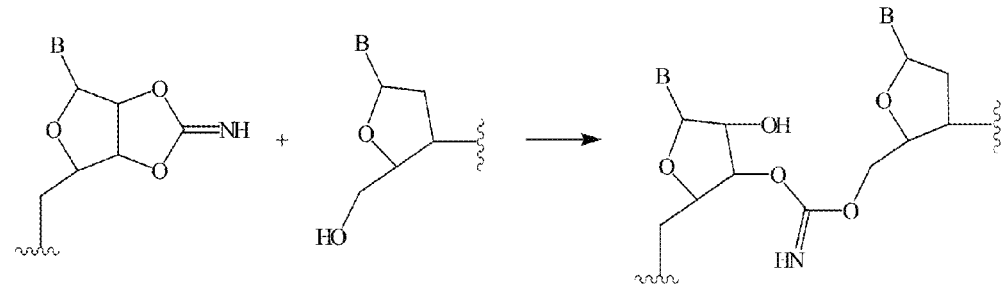
Figure 8:
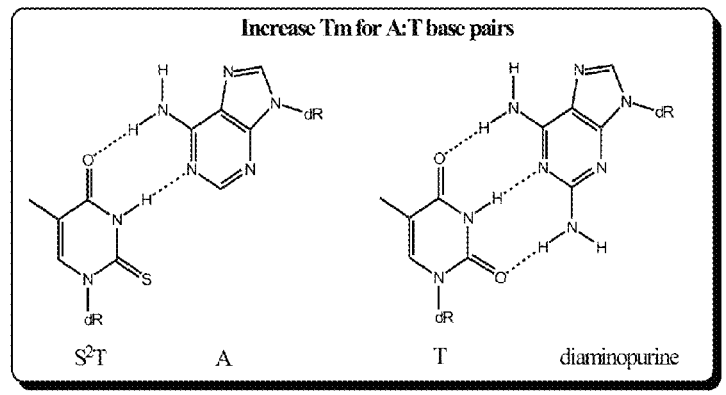
FIGS. 8A-8B depict various nucleotide substitutions that increase Tm (A) and increase specificity (B).
Figure 8:
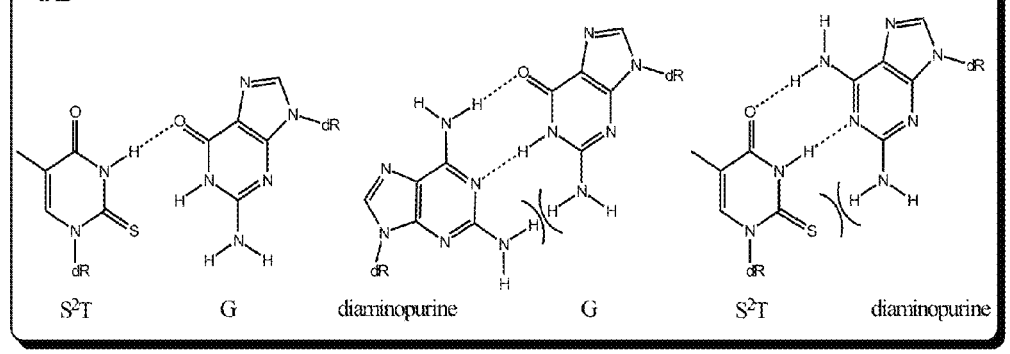

Phosphodiester mimetics, e.g. aldehydes generated by periodate, Schiff's base intermediates formed on reaction with primary amines and the like, are depicted in FIG. 7. The chemical ligation reactions have a broader range of substrates so that the variation in binding as a function of template, anchor and probe can be altered, for example, as depicted in FIG. 8. Certain mimetics may also be suitable for protein-ligase or polymerase reactions.

The probe can substitute one or more T to $S^2T$, which binds better to A (higher Tm) on the template strand. Similarly, one or more A's in the probe can be replaced by diaminopurine (DAP) which binds better to T on the template strand. Due to its bulk and lowered hydrogen-bonding ability, the $S^2T$ is also better at discriminating against G or DAP in the probe molecules or G in the template molecules (James et al. (1997) *Chem. Biol.* 4:595).

Example III

Preactivated Phosphates

Figure 5:
FIGS. 5A-5B schematically depict chemical ligation using pre-activated phosphates. A) first round hybridization. Template, lower strand 1-12; Probe with phosphates at both ends, upper right, 1-6. B) second round hybridization. As part A) after addition of the first probe depicting efficient reaction with the remaining phosphate (upper) and failure of a second probe to react in the first position (even in the absence of pair mismatches) (lower).
Figure 5:
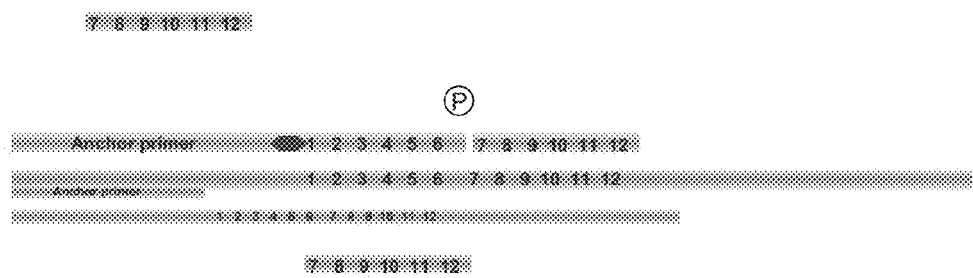

In certain exemplary embodiments, preactivated phosphates are used to accelerate ligation reactions. Preactivated phosphates can be present on, for example, one or more of the 3' and/or 5' ends of an oligonucleotide sequence. If the oligonucleotide sequence has preactivated phosphates at both ends, this permits a second round of ligation (e.g., sequencing by chemical ligation) without need for a potentially inefficient deprotection step. The second round probe would have a non-phosphate OH, SH or $NH_2$ moiety at its 5' end if the original anchor is on the 5' end, and/or a non-phosphate OH, SH or $NH_2$ moiety at its 3' end of the second probe if the original anchor is to the 3' end of the template region to be sequenced. Without intending to be bound by scientific theory, an oligonucleotide sequence having two non-phosphate ends could serve this purpose as well. FIGS. 5A-5B schematically depict chemical ligation using preactivated phosphates. Ligation using oligonucleotide sequences having one or more preactivated phosphates is applicable for use with any combination of the four classes of fast and accurate chemical reactions described herein: 1) cyanogen bromide-based reactions; 2) carbodiimide-based reactions; 3) amidate-based reactions; and 4) phosphodiester mimetic-based reactions.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention.

What is claimed is:

1. A method of ligating a probe to a reference oligonucleotide comprising the steps of:
providing a reference oligonucleotide having an anchor primer bound thereto;
providing a first probe oligonucleotide having a preactivated chemical ligation compound attached thereto;
allowing the first probe oligonucleotide to hybridize to the reference oligonucleotide; and
allowing the preactivated chemical ligation compound to mediate ligation between the hybridized first probe oligonucleotide and the anchor primer, wherein the preactivated chemical ligation compound is a phosphoramidate.

2. A method of ligating a probe to a reference oligonucleotide comprising the steps of:
providing a reference oligonucleotide having an anchor primer bound thereto;
providing a first probe oligonucleotide having a preactivated chemical ligation compound attached thereto;
allowing the first probe oligonucleotide to hybridize to the reference oligonucleotide; and
allowing the preactivated chemical ligation compound to mediate ligation between the hybridized first probe oligonucleotide and the anchor primer, wherein the preactivated chemical ligation compound is a phosphoramidate which includes an R group selected from the group consisting of pyridine, aniline, imidazole, ethanolamine, azaoxybenzotriazolide, N-oxysuccinimide and succinimide.

3. The method of claim 1, wherein the first probe oligonucleotide further comprises one or more $S^2T$ molecules.

4. The method of claim 1, wherein one or more thymines of the first probe oligonucleotide are replaced by one or more $S^2T$ molecules.

5. The method of claim 1, wherein the first probe oligonucleotide further comprises one or more diaminopurines.

6. The method of claim 1, wherein one or more adenines of the first probe oligonucleotide are replaced by one or more diaminopurines.

7. A method of ligating a probe to a reference oligonucleotide comprising the steps of:
providing a reference oligonucleotide having an anchor primer bound thereto;
providing a first probe oligonucleotide having two preactivated chemical ligation compounds attached thereto;
allowing the first probe oligonucleotide to hybridize to the reference oligonucleotide; and
allowing the preactivated chemical ligation compound to mediate ligation between the hybridized first probe oligonucleotide and the anchor primer, wherein the preactivated chemical ligation compound is a phosphoramidate.

8. A method of ligating a probe to a reference oligonucleotide comprising the steps of:
providing a reference oligonucleotide having an anchor primer bound thereto;
providing a first probe oligonucleotide having a preactivated chemical ligation compound attached thereto;
allowing the first probe oligonucleotide to hybridize to the reference oligonucleotide;
allowing the preactivated chemical ligation compound to mediate ligation between the hybridized first probe oligonucleotide and the anchor primer;
providing a second probe oligonucleotide;
allowing the second probe oligonucleotide to hybridize to the reference oligonucleotide; and
allowing the preactivated chemical ligation compound to mediate ligation between the hybridized second probe oligonucleotide and the hybridized first probe oligonucleotide, wherein the preactivated chemical ligation compound is a phosphoramidate.

9. A method of ligating a probe to a reference oligonucleotide comprising the steps of:
providing a reference oligonucleotide having an anchor primer bound thereto;
providing a first probe oligonucleotide having a preactivated chemical ligation compound attached thereto;
allowing the first probe oligonucleotide to hybridize to the reference oligonucleotide;
allowing the preactivated chemical ligation compound to mediate ligation between the hybridized first probe oligonucleotide and the anchor primer;
providing a second probe oligonucleotide;

allowing the second probe oligonucleotide to hybridize to the reference oligonucleotide, wherein the second probe oligonucleotide has a preactivated chemical ligation compound attached thereto; and allowing the preactivated chemical ligation compound to mediate ligation between the hybridized second probe oligonucleotide and the hybridized first probe oligonucleotide, wherein the preactivated chemical ligation compound is a phosphoramidate.

10. A method of assembling a polynucleotide sequence comprising the steps of:

providing a plurality of overlapping oligonucleotides, at least a portion of which have a preactivated chemical ligation compound attached thereto;

allowing hybridization of at least a portion of the overlapping oligonucleotides to each other; and allowing the preactivated chemical ligation compounds to mediate ligation between adjacent 5' and 3' ends of hybridized oligonucleotides to assemble a polynucleotide sequence, wherein the preactivated chemical ligation compound is a phosphoramidate.

11. The method of claim 10, wherein the polynucleotide sequence is DNA.

12. The method of claim 11, wherein the DNA is selected from the group consisting of a vector, a gene, a gene fragment, an exon, an intron and an intergenic DNA sequence.

13. A method of ligating a first oligonucleotide to a second oligonucleotide comprising the steps of:

providing a first oligonucleotide having a preactivated chemical ligation compound attached thereto;

providing a second oligonucleotide; and allowing the preactivated chemical ligation compound to mediate ligation between the first oligonucleotide and the second oligonucleotide, wherein the preactivated chemical ligation compound is a phosphoramidate.

14. The method of claim 13, further comprising the step of allowing the first oligonucleotide to bind a reference oligonucleotide.

15. The method of claim 14, wherein the reference oligonucleotide is attached to a substrate.

16. A method of ligating a probe to a reference oligonucleotide comprising the steps of:

providing a reference oligonucleotide having an anchor primer bound thereto;

providing a first probe oligonucleotide having two preactivated chemical ligation compounds attached thereto;

allowing the first probe oligonucleotide to hybridize to the reference oligonucleotide; and allowing the preactivated chemical ligation compound to mediate ligation between the hybridized first probe oligonucleotide and the anchor primer, wherein the preactivated chemical ligation compound is a member selected from the group consisting of a cyanogen bromide-based compound, a carbodiimide-based compound, an amidate-based compound and an imine.

17. The method of claim 16, wherein the cyanogen bromide-based compound is a phosphocyanate.

18. The method of claim 17, wherein the phosphocyanate is 2-(N-Morpholino)Ethane Sulfonic Acid-cyanogen.

19. The method of claim 16, wherein the carbodiimide-based compound is an O-phospho-isocarbamide compound.

20. The method of claim 19, wherein the O-phospho-isocarbamide compound is phospho-1-Ethyl-3-[3-Dimethylaminopropyl]Carbodiimide.

21. The method of claim 16, wherein the amidate-based compound is a phosphoramidate.

22. The method of claim 21, wherein the phosphoramidate includes an R group selected from the group consisting of pyridine, aniline, imidazole, ethanolamine, azaoxybenzotriazolide, N-oxysuccinimide and succinimide.

23. The method of claim 16, wherein the first probe oligonucleotide further comprises one or more $S^2T$ molecules.

24. The method of claim 16, wherein one or more thymines of the first probe oligonucleotide are replaced by one or more $S^2T$ molecules.

25. The method of claim 16, wherein the first probe oligonucleotide further comprises one or more diaminopurines.

26. The method of claim 16, wherein one or more adenines of the first probe oligonucleotide are replaced by one or more diaminopurines.

27. The method of claim 16, further comprising the steps of:

providing a second probe oligonucleotide;

allowing the second probe oligonucleotide to hybridize to the reference oligonucleotide; and allowing the preactivated chemical ligation compound to mediate ligation between the hybridized second probe oligonucleotide and the hybridized first probe oligonucleotide.

28. The method of claim 27, wherein the second probe oligonucleotide has a preactivated chemical ligation compound attached thereto.

29. A method of assembling a polynucleotide sequence comprising the steps of:

providing a plurality of overlapping oligonucleotides having at least a portion of which have a preactivated chemical ligation compound attached thereto and at least one of which has two preactivated chemical ligation compounds attached thereto;

allowing hybridization of at least a portion of the overlapping oligonucleotides to each other; and allowing the preactivated chemical ligation compounds to mediate ligation between adjacent 5 and 3' ends of hybridized oligonucleotides to assemble a polynucleotide sequence, wherein the preactivated chemical ligation compound is a member selected from the group consisting of a cyanogen bromide-based compound, a carbodiimide-based compound, an amidate-based compound and an imine.

30. The method of claim 29, wherein the polynucleotide sequence is DNA.

31. The method of claim 30, wherein the DNA is selected from the group consisting of a vector, a gene, a gene fragment, an exon, an intron and an intergenic DNA sequence.

32. A method of ligating a first oligonucleotide to a second oligonucleotide comprising the steps of:

providing a first oligonucleotide having two preactivated chemical ligation compounds attached thereto;

providing a second oligonucleotide; and allowing the preactivated chemical ligation compound to mediate ligation between the first oligonucleotide and the second oligonucleotide, wherein the preactivated chemical ligation compound is a member selected from the group consisting of a cyanogen bromide-based compound, a carbodiimide-based compound, an amidate-based compound and an imine.

33. The method of claim 32, further comprising the step of allowing the first oligonucleotide to bind a reference oligonucleotide.

34. The method of claim 32, wherein the reference oligonucleotide is attached to a substrate.

35. The method of claim 2, wherein the first probe oligonucleotide further comprises one or more $S^2T$ molecules.

36. The method of claim 2, wherein one or more thymines of the first probe oligonucleotide are replaced by one or more $S^2T$ molecules.

37. The method of claim 2, wherein the first probe oligonucleotide further comprises one or more diaminopurines.

38. The method of claim 2, wherein one or more adenines of the first probe oligonucleotide are replaced by one or more diaminopurines.

39. The method of claim 2, wherein the first probe oligonucleotide has two preactivated chemical ligation compounds attached thereto.

40. The method of claim 2, further comprising the steps of:
providing a second probe oligonucleotide;
allowing the second probe oligonucleotide to hybridize to the reference oligonucleotide; and
allowing the preactivated chemical ligation compound to mediate ligation between the hybridized second probe oligonucleotide and the hybridized first probe oligonucleotide.

41. The method of claim 40, wherein the second probe oligonucleotide has a preactivated chemical ligation compound attached thereto.

42. The method of claim 7, wherein the first probe oligonucleotide further comprises one or more $S^2T$ molecules.

43. The method of claim 7, wherein one or more thymines of the first probe oligonucleotide are replaced by one or more $S^2T$ molecules.

44. The method of claim 7, wherein the first probe oligonucleotide further comprises one or more diaminopurines.

45. The method of claim 7, wherein one or more adenines of the first probe oligonucleotide are replaced by one or more diaminopurines.

46. The method of claim 7, further comprising the steps of:
providing a second probe oligonucleotide;
allowing the second probe oligonucleotide to hybridize to the reference oligonucleotide; and
allowing the preactivated chemical ligation compound to mediate ligation between the hybridized second probe oligonucleotide and the hybridized first probe oligonucleotide.

47. The method of claim 46, wherein the second probe oligonucleotide has a preactivated chemical ligation compound attached thereto.

48. The method of claim 8, wherein the first probe oligonucleotide further comprises one or more $S^2T$ molecules.

49. The method of claim 8, wherein one or more thymines of the first probe oligonucleotide are replaced by one or more $S^2T$ molecules.

50. The method of claim 8, wherein the first probe oligonucleotide further comprises one or more diaminopurines.

51. The method of claim 8, wherein one or more adenines of the first probe oligonucleotide are replaced by one or more diaminopurines.

52. The method of claim 9, wherein the first probe oligonucleotide further comprises one or more $S^2T$ molecules.

53. The method of claim 9, wherein one or more thymines of the first probe oligonucleotide are replaced by one or more $S^2T$ molecules.

54. The method of claim 9, wherein the first probe oligonucleotide further comprises one or more diaminopurines.

55. The method of claim 9, wherein one or more adenines of the first probe oligonucleotide are replaced by one or more diaminopurines.

* * * * *